United States Patent [19]

Hirano et al.

[11] Patent Number: 4,985,348
[45] Date of Patent: Jan. 15, 1991

[54] PROCESS FOR PHOTOGRAPHIC DEVELOPMENT PROCESSING

[75] Inventors: Mitsunori Hirano; Masato Hirano; Morio Yagihara; Hisashi Okada, all of Kanagawa, Japan

[73] Assignee: Fuji Photo Film Co., Ltd., Kanagawa, Japan

[21] Appl. No.: 306,139

[22] Filed: Feb. 6, 1989

[30] Foreign Application Priority Data

Feb. 4, 1988 [JP] Japan .................................. 63-24123

[51] Int. Cl.$^5$ ............................................. G03C 5/305
[52] U.S. Cl. ....................................... 430/434; 430/488; 430/489
[58] Field of Search ............... 430/264, 440, 488, 489, 430/434

[56] References Cited

U.S. PATENT DOCUMENTS

| | | | |
|---|---|---|---|
| 4,371,610 | 1/1983 | Toyoda et al. | 430/445 |
| 4,717,648 | 1/1988 | Ueda et al. | 430/379 |
| 4,772,546 | 9/1988 | Deguchi et al. | 430/603 |

FOREIGN PATENT DOCUMENTS 0155690 9/1985 European Pat. Off. .
1930338 12/1970 Fed. Rep. of Germany .

OTHER PUBLICATIONS

European Search Report.
Patent Abstracts of Japan, vol. 7, No. 231 (p. 229)-J-P-A-58 120 247.

*Primary Examiner*—Paul R. Michl
*Assistant Examiner*—Janet C. Baxter
*Attorney, Agent, or Firm*—Sughrue, Mion, Zinn, Macpeak & Seas

[57] ABSTRACT

A process for development-processing a black-and-white silver halide light-sensitive material is disclosed, which comprises using a developer containing at least one compound represented by formulae (I) and (II):

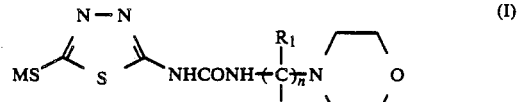

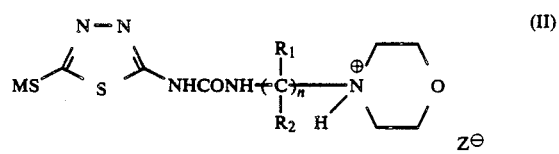

wherein
$R_1$ and $R_2$ each represents hydrogen atom, an alkyl group or an aryl group;
M represents hydrogen atom, an alkali metal atom, an alkaline earth metal atom, a quaternary ammonium salt, a quaternary phosphonium salt, an amidino group or a group capable of being converted to hydrogen or an alkali metal atom under alkaline conditions;
n represents an integer of 1 or more; and
$Z^\ominus$ represents an anion.

9 Claims, No Drawings

PROCESS FOR PHOTOGRAPHIC DEVELOPMENT PROCESSING

FIELD OF THE INVENTION

This invention relates to a process for development processing silver halide black-and-white photographic materials and, more particularly, to a development-processing process which does not cause generation of silver sludge even when a developer containing a sulfite or a silver halide solvent in a high concentration is used.

BACKGROUND OF THE INVENTION

In processing photographic materials containing at least one silver halide-containing layer, development is usually conducted in the presence of hydroquinone, catechol, aminophenol, phenylenediamine, pyrazolidone, reductone or hydroxylamine derivative. Development is usually conducted in an alkaline medium and, in this situation, the developer solution in many cases further contains such additives as sulfites for stabilization, pH-buffering substances and anti-foggants. In order to increase the stability of the developer, it is particularly important from a practical view to add a highly concentrated sulfite. In some cases, development of photographic materials is conducted in the presence of a silver halide solvent for obtaining special effects. For example, it has been known to add a divalent sulfur compound such as a mercapto compound, a thioether or thioamide, a thiocyanate, a highly concentrated sulfite or thiosulfate for the abovedescribed purpose. Developers containing such additives are known as fine grain developers or intermediate grain developers (Grant Haist, *Modern Photoqraphic Processing*, published by Wiley-Interscience in 1979, pp. 225–229).

Another important embodiment of using the silver halide solvent is a mono-bath develop-fixing solution described in G. Haist, *Monobath Manual*, published by Morgan Co. in 1960. Developers containing the silver halide solvent or a highly concentrated sulfite usually dissolve a comparatively large amount of silver salt out of silver salt layers of photographic materials. Silver salts dissolved in the developer are then reduced with a developing agent to become fine metallic silver, forming a sludge in the solution. In the case of conducting development using a developer containing a large amount of the silver halide solvent by means of a conveyingtype automatic developing machine, a large amount of silver salt is dissolved, and hence a serious problem of deposition of the sludge arises. This deposition is particularly serious when the processing is conducted at high temperatures. The sludge deposits as massive pieces on various positions of the conveying-type automatic developing machine for use in development processing, such as rollers and belts, staining the surface of films or flaw films, thus deteriorating the finished quality of photographic pictures. Therefore, it is particularly important with photographic light-sensitive materials for printing use to decrease the silver stain of films to the greatest extent possible.

As antisludging agents for such purpose, there have been known 2-mercapto-1,3,4-thiadiazoles (British Patent No. 940,169), 2-mercapto-1,3,4-oxadiazoles or 1-phenyl-5-mercaptotetrazole (U.S. Pat. No. 3,173,789), DL6,8-dithiooctanoic acid (U.S. Pat. No. 3,318,701), 1-mercaptobenzoic acid (British Patent No. 1,144,481) aliphatic mercaptocarboxylic acids (U.S. Pat. No. 3,628,955), L-thiazolidine-4-carboxylic acid (*J. Photogr. Sci.*, 13, 233 (1965)), divalent sulfur compounds (JP-A-No. 52-36029 (the term "JP-A" as used herein means an "unexamined published Japanese patent application")), 2-mercaptobenzoxazole, 2-mercaptobenzimidazole (*Photogr. Sci. Eng.*, 20, 220 (1976)), etc.

However, all of these compounds are still unsatisfactory as antisludging agents for use in photographic developers, particularly developers which contain a compound capable of dissolving silver halide, such as a highly concentrated sulfite. Many of the mercapto compounds rapidly lose their antisludging effect as a result of air oxidation or a reduction reaction between a disulfide compound produced by the oxidation and a sulfite ion. In the case when a large amount of silver salt is dissolved, sparingly soluble silver salts are formed to stain films, degree of which, however, depends upon the added amount. In some cases, they inhibit development when added in large amounts. Further, some compounds give an offensive smell. The above-described compounds also have such a low water solubility that it is difficult to add them in amounts necessary for preventing sludge formation.

SUMMARY OF THE INVENTION

An object of the present invention is to provide a process of photographic development whereby the generation of sludge in a developer for silver halide photographic materials is prevented.

Another object of the present invention is to provide a process for obtaining photographic images with particularly excellent finished quality by processing black-and-white light-sensitive materials using an automatic developing machine.

A further object of the present invention is to provide a process for processing black-and-white light-sensitive materials using a developer containing an antisludging compound having excellent solubility and stability in the developer.

The above described objects can be attained by processing black-and-white silver halide photographic materials using a developer containing a compound represented by formula (I) or (II):

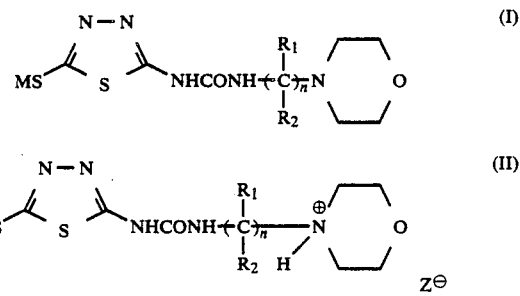

In the above formulae, $R_1$ and $R_2$ each independently represents hydrogen atom, an alkyl group or an aryl group. The alkyl group can be unsubstituted as well as including those which possess one or more substituents, and is preferably a lower alkyl group, and most preferably methyl group. The aryl group can be unsubstituted as well as including those which possess one or more substituents, and is preferably a phenyl group. $R_1$ and $R_2$ each more preferably represents hydrogen atom or methyl group.

M represents hydrogen atom, an alkali metal atom (for example, sodium, potassium), an alkaline earth metal atom (for example, calcium, magnesium), a quaternary ammonium group (for example, trimethylammonium, dimethylbenzylammonium) a quaternary phosphonium group (for example, tetrabutylphosphonium, trimethylbenzylphosphonium), a group capable of being converted to hydrogen atom or an alkali metal atom under alkaline conditions (for example, acetyl, cyanoethyl, methanesulfonylethyl) or an amidino group. M preferably represents hydrogen atom or an alkali metal atom.

n represents an integer of 1 or more. n preferably represents an integer of 1 to 4, more preferably 3.

$Z^{\ominus}$ represents an anion such as a halide ion (for example, $Cl^{\ominus}$, $Br^{\ominus}$, $I^{\ominus}$), a sulfonato ion (for example, trifluoromethanesulfonato, p-toluenesulfonato, benzenesulfonato, p-chlorobenzenesulfonato), a sulfato ion (for example, ethylsulfato, methylsulfato), perchlorato ion, or tetrafluoroborato ion.

DETAILED DESCRIPTION OF THE INVENTION

Specific examples of the compounds represented by formula (I) or (II) are illustrated below.

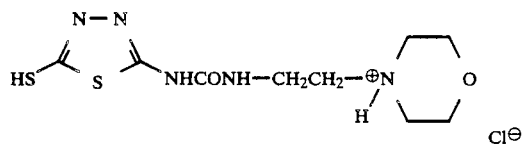
1.

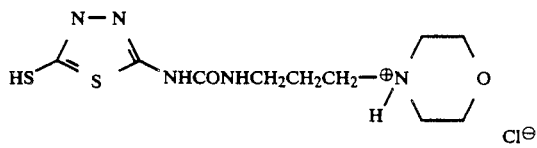
2.

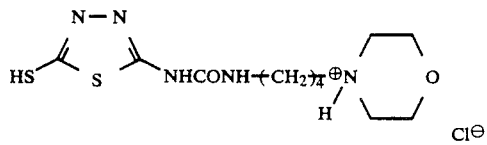
3.

4.

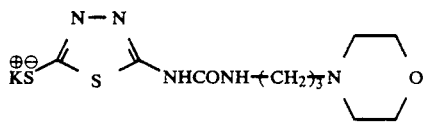
5.

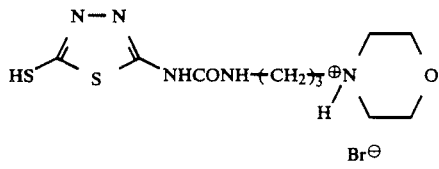
6.

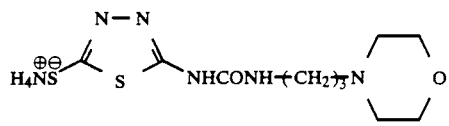
7.

8.

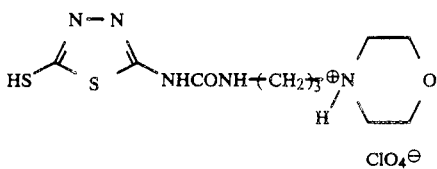
9.

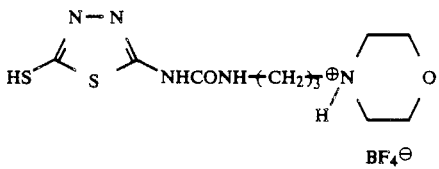
10.

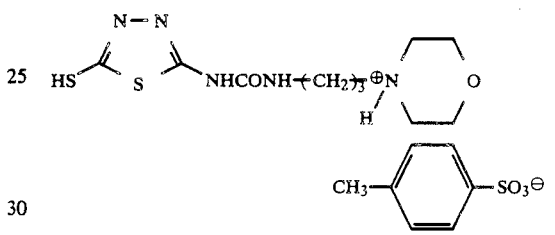
11.

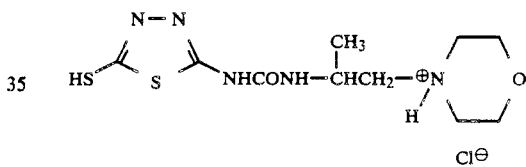
12.

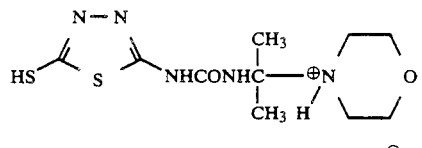
13.

The compounds of the present invention can generally be synthesized according to the following process

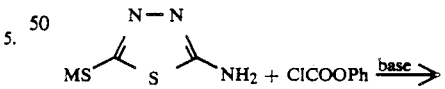

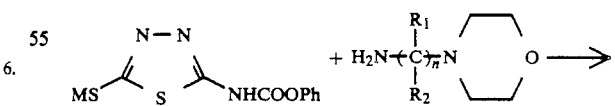

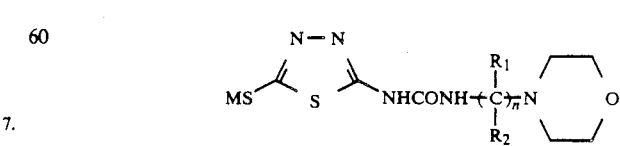

The process for synthesizing the compounds of formulae (I) and (II) is described below by reference to Synthesis Example of a typical compound.

(Synthesis Example) Synthesis of Illustrative Compound 2

(1) Synthesis of 2-mercapto-5-phenoxycarbonylamino1,3,4-thiadiazole 61 g of 2-amino-5-mercapto-1,3,4-thiadiazole were dissolved in 230 ml of dimethylacetamide, and 40.8 ml of pyridine were added thereto. The resulting solution was cooled to a temperature not higher than 0° C., and 79 g of phenyl chlorocarbonate were added dropwise thereto. After completion of the dropwise addition, the solution was stirred for 1.5 hours at a temperature not higher than 0° C., and the reaction mixture was then poured into 1 liter of ice-water. Precipitated crystals were collected by filtration and recrystallized from acetonitrile to obtain the desired product.

Yield: 92 g (79%)

(2) Synthesis of illustrative compound 2

33.4 g of the compound obtained in (1) were stirred and dissolved in 260 ml of ethanol, and 22.8 g of 1-(3-aminopropyl)morpholine were added dropwise thereto. After stirring the solution for 6 hours, 16.7 ml of concentrated hydrochloric acid were added thereto, followed by stirring for an additional 30 minutes. Precipitated crystals were collected by filtration and recrystallized from water to obtain the desired product. Yield 27 g (60%); Melting point: 253°-254.5° C. (decomposed)

Optimum amounts of these compounds to be added to the developer vary depending upon kinds of the compounds but preferably range from $1 \times 10^{-2}$ to $1 \times 10^{-5}$, more preferably from $5 \times 10^{-3}$ to $1 \times 10^{-4}$, mol/liter of the developer.

In the development processing solution of the present invention, ordinary black-and-white photographic developing agents such as hydroquinone, alkylhydroquinones (for example, butylhydroquinone, methylhydroquinone, dimethylhydroquinone), catechol, pyrazole, chlorohydroquinone, dichlorohydroquinone, alkoxyhydroquinones (for example, methoxyhydroquinone, ethoxyhydroquinone), aminophenol developing agents (for example, N-methyl-p-aminophenol, 2,4-diaminophenol), ascorbic acid developing agent, N-methyl-p-aminophenol sulfate, pyrazolones (for example, 4-aminopyrazolone), and 3-pyrazolidone developing agents (for example, 1-phenyl-3-pyrazolidone, 1-phenyl-4,4-dimethyl-3pyrazolidone, 1-phenyl-5-methyl-3-pyrazolidone, 1-phenyl-4-methyl-3-pyrazolidone, 1,5-diphenyl-3pyrazolidone, 1-p-tolyl 3-pyrazolidone, 1-phenyl-2-acetyl-4,4 dimethyl-3-pyrazolidone, 1-p-hydroxyphenyl4,4-dimethyl-3-pyrazolidone, 1-(2-benzothiazolyl)-3pyrazolidone, 3-acetoxy-1-phenyl-3-pyrazolidone) may be used alone or in combination.

Among these, 3-pyrazolidone developing agents are particularly useful. They may be wholly or partly incorporated into photographic materials because 3-pyrazolidone developing agents may be added directly to emulsion layers themselves or to layers adjacent to the emulsion layers. However, with developers for high contrast, high-speed photographic light-sensitive materials containing a sulfite, it is generally desirable to add enough of a pyrazolidone developing agent in an aqueous developer for effectively conducting rapid processing.

In particular, a combination of hydroquinone and a 3-pyrazolidone or a combination of hydroquinone and an aminophenol is useful for rapid processing at elevated temperatures.

Developers are usually used in an alkaline state, but the kind and amount of alkali agents to be used are not particularly limited. In order to prevent oxidation of developer, commonly used alkali metal sulfites such as sodium sulfite, potassium sulfite and potassium metabisulfite may be used. The compound represented by general formula (I) or (II) exhibits a particularly remarkable antisludging effect when it is used in a developer containing 13 g or more, particularly 20 g or more, of free sulfite ion per liter. A large antisludging effect is also obtained when the compound is used in a developer containing, for example, a mercapto compound, thioether, thioamide or thiocyanate as a water-soluble silver halide solvent.

Formation of sludge is substantially prevented by the developing process of the present invention. Formation of fog can also be substantially prevented by using a compound represented by general formula (III) in combination with the compound of the present invention represented by general formula (I) or (II):

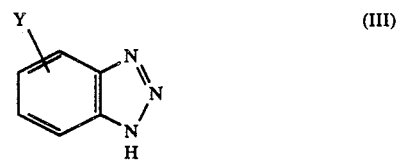
(III)

In the above formula, Y represents hydrogen atom, a halogen atom (for example, chlorine, bromine), an acylamino group containing from 2 to 10 carbon atoms (for example, acetylamino), or an alkyl group containing from 1 to 10 carbon atoms (for example, methyl, heptyl). The alkyl moiety in Y preferably contains from 1 to 3 carbon atoms.

Specific examples of the compounds represented by formula (III) are illustrated below.

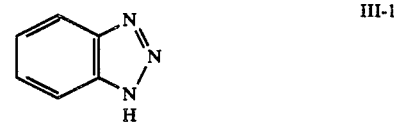
III-1

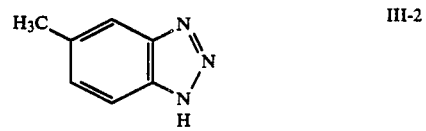
III-2

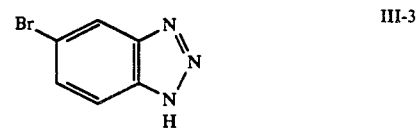
III-3

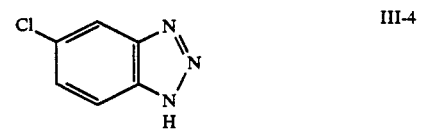
III-4

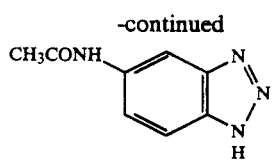

The benzotriazole compounds represented by general formula (III) may be synthesized by the methods described in *Organic Synthesis, Col. Vol.* 3, p. 106; *J. Chem. Soc.* Vol 119 (1921), P. 2088-2094, ibid., (1931), pp. 1474-1478, etc., for example. The compounds represented by general formula (III) are preferably used in amounts of $1 \times 10^{-3}$ mol/liter to $1 \times 10^{-2}$ mol/liter and more preferably from $1 \times 10^{-4}$ mol/liter to $7 \times 10^{-3}$ mol/liter of the developer.

Other developer components include pH buffers such as a water-soluble acid (for example, acetic acid, boric acid), an alkali (for example, sodium carbonate or sodium hydroxide), and a salt; and development-adjusting agents such as an alkali halide (for example, potassium bromide). Certain kinds of alkali agents function not only as agents for rendering a developer alkaline but also as pH buffers and development-adjusting agents. The developer may further contain an antioxidant such as ascorbic acid or a primary or secondary alkanolamine (for example, diethanolamine), water softeners such as ethylenediaminetetraacetic acid or nitrilotriacetic acid, polyalkylene oxides, amine compounds, and organic solvents such as triethylene glycol, dimethylformamide, methyl alcohol and cellosolves.

In the present invention, it suffices that these necessary components for developers are incorporated upon use, and they may be in any form before being compounded to prepare a processing solution to be used, such as a mixture of solid components, a concentrated solution, a solution, an emulsion or a suspension. For example, components of a developer may be separated into several portions and stored in the same or different forms, or may be in a previously compounded powdery or liquid state.

The compounded components may, if necessary, be dissolved in, or diluted with, water to prepare an aqueous solution to be used.

In practicing the development processing according to the present invention, the temperature of the developer is usually selected to be between 18° C. and 50° C., more preferably between 25° C. and 43° C. The pH of the developer is suitably from 9.0 to 12.0. After development processing, photographic materials are fixed, washed with water, and dried in a conventional manner to obtain black-and-white images.

The process of the present invention is particularly adaptable for rapid processing using an automatic developing machine. As the automatic developing machine, any one of roller-conveying type, belt-conveying type, etc. may be used. Processing time may be short, the total time being within 2 minutes, and satisfactory effects can be obtained even when the processing time is within 100 seconds total during which rapid development is conducted within 15 to 60 seconds.

Light-sensitiv,e materials to be processed according to the process of the present invention can be used for a variety of purposes and the silver halide in light-sensitive layers can be selected from silver chloride, silver chlorobromide, silver chloroiodobromide, silver bromide, silver iodobromide, etc. Particularly remarkable effects of the present invention are obtained when light sensitive materials comprising a silver halide emulsion containing no silver iodide or containing only a small amount (for example, up to 2 mol%) of silver iodide. Silver halide emulsions of light-sensitive materials to be used in the present invention may be of the negative-working type or direct-positive type.

The development-processing process of the present invention is more preferably applied to light-sensitive materials providing high contrast.

In the present invention, the term "high contrast" means a gradation of 4 or more in gamma.

Among light-sensitive materials for obtaining such high contrast negative images, those light-sensitive materials using hydrazine derivatives which are described in U.S. Pat. Nos. 4,224,401, 4,168,977, 4,166,742, 4,311,781, 4,272,606, 4,211,857, and 4,243,739. and those light-sensitive materials using tetrazoliums which are described in JP-A- No. 52-18317, JP-A No. 53-17719, and JP-A- No. 53-17720 are preferred.

Preferred examples of the hydrazine derivatives to be used in the present invention are compounds represented by general formula (IV):

$$R^1-NHNH-G-R^2 \qquad (IV)$$

wherein $R_1$ represents an aliphatic group or an aromatic group; $R^2$ represents hydrogen atom, a substituted or unsubstituted alkyl group, a substituted or unsubstituted aryl group, a substituted or unsubstituted alkoxy group, or a substituted o unsubstituted aryloxy group; and G represents a carbonyl group, a sulfonyl group, a sulfoxy group, a sulforyl group, or an N-substituted or unsubstituted iminomethylene group.

In general formula (IV), the aliphatic group represented by $R_1$ contains preferably from 1 to 30 carbon atoms and is preferably a straight, branched or cyclic alkyl group containing from 1 to 20 carbon atoms. The branched alkyl group may be cyclized to form a saturated hetero ring containing 1 or more hetero atoms. The alkyl group may have a substituent or substituents such as an aryl group, an alkoxy group, a sulfoxy group, a sulfonamido group or a carbonamido group.

The aromatic group represented by $R_1$ is a monocyclic or bicyclic aryl or unsaturated heterocyclic group. The unsaturated heterocyclic group may be fused with a mono- or bicyclic aryl group to form a heteroaryl group.

For example, there are illustrated those containing a benzene ring, a naphthalene ring, a pyridine ring, a pyrimidine ring, an imidazole ring, a pyrazole ring, a quinoline ring, an isoquinoline ring, a benzimidazole ring, a thiazole ring, or a benzothiazole ring, with those which contain a benzene ring being preferable.

An aryl group is particularly preferable as $R^1$. The aryl group or unsaturated heterocyclic group represented by $R^1$ may be substituted. Typical substituents include a straight, branched or cyclic alkyl group (containing preferably from 1 to 20 carbon atoms), an aralkyl group (containing from 1 to 3 carbon atoms in the alkyl moiety and containing one or two rings), an alkoxy group (containing preferably from 1 to 20 carbon atoms), a substituted amino group (an amino group substituted by an alkyl group or groups containing from 1 to 20 carbon atoms being preferred), an acylamino group (containing preferably from 2 to 30 carbon atoms), a sulfonamido group (containing preferably from 1 to 30 carbon atoms), and a ureido group (containing preferably from 1 to 30 carbon atoms).

The alkyl group represented by $R_2$ is preferably an alkyl group containing from 1 to 4 carbon atoms which may have one or more substituents such as a halogen atom, a cyano group, a carboxyl group, a sulfo group, an alkoxy group or a phenyl group.

The optionally substituted aryl group represented by $R^2$ is a mono- or bicyclic aryl group containing, for example, a benzene ring. This aryl group may be substituted by, for example, a halogen atom, an alkyl group, a cyano group, a carboxyl group or a sulfo group.

The optionally substituted alkoxy group represented by $R^2$ is an alkoxy group containing from 1 to 8
sented by $R_2$ carbon atoms which may be substituted by, for example, a halogen atom or an aryl group.

The optionally substituted aryloxy group represented by $R_2$ is preferably monocyclic, and examples of the substituents include a halogen atom.

When G represents a carbonyl group, $R_2$ preferably represents hydrogen atom, methyl group, methoxy group, ethoxy group or a substituted or unsubstituted phenyl group, with hydrogen atom being particularly preferred.

When G represents a sulfonyl group, $R_2$ preferably represents methyl group, ethyl group, phenyl group, or 4-methylphenyl group, with methyl group being particularly preferred.

When G represents a sulforyl group, $R_2$ preferably represents methoxy group, ethoxy group, butoxy group, phenoxy group or phenyl group, with phenoxy group being particularly preferred.

When G represents a sulfoxy group, $R_2$ preferably represents cyanobenzyl group or methylthiobenzyl group, and when G represents an N-substituted or unsubstituted iminomethylene group, $R_2$ preferably represents methyl group, ethyl group, or a substituted or unsubstituted phenyl group.

$R_1$ or $R_2$ may have a ballast group which is commonly used in immobile photographic additives such as couplers. The ballast group is a group containing 8 or more carbon atoms and is relatively photographically inert. It may be selected from among an alkyl group, an alkoxy group, a phenyl group, an alkylphenyl group, a phenoxy group and an alkylphenoxy group, for example, capable of strengthening adsorbing ability onto the silver halide grain surface. As such adsorptive groups there are illustrated those described in U.S. Pat. No. 4,385,108, such as a thiourea group, a heterocyclic thioamido group, a mercapto-heterocyclic group and a triazole group.

G in general formula (IV) most preferably represents a carbonyl group.

Specific examples of the compounds represented by general formula (IV) are illustrated below which, however, do not limit the present invention in any way.

(1)

(2)

(3)

(4)

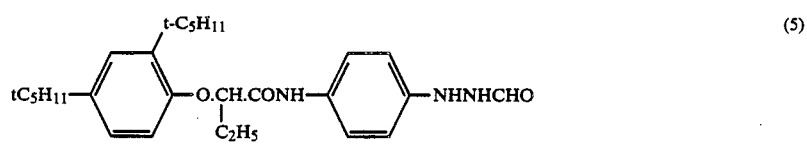

(5)

(6)

(7)

-continued
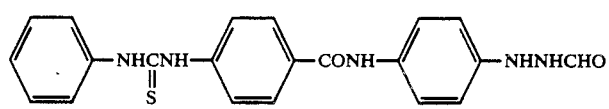 (8)
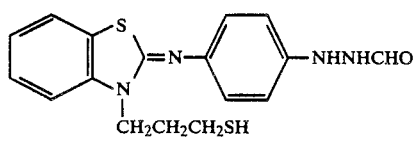 (9)
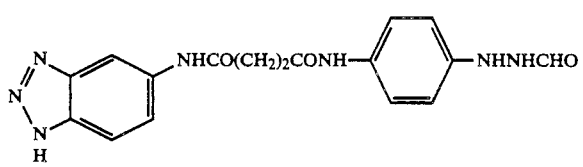 (10)
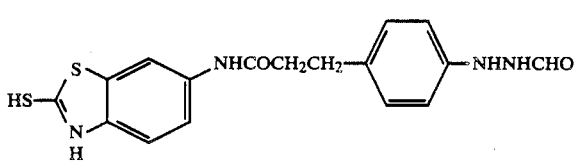 (11)
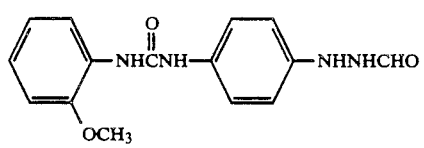 (12)
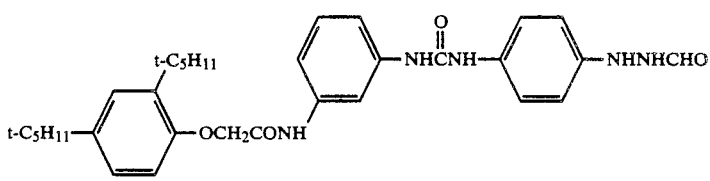 (13)
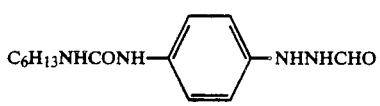 (14)
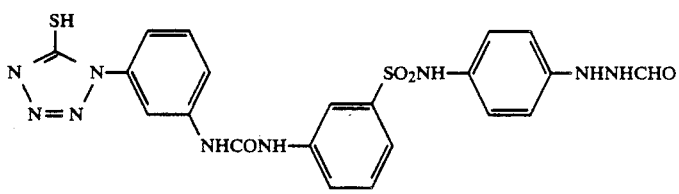 (15)
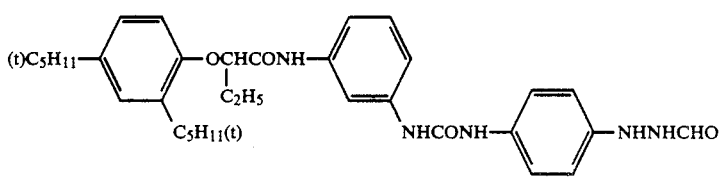 (16)
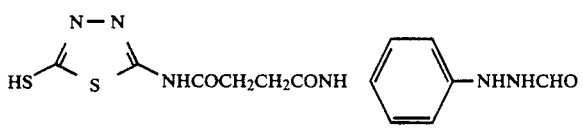 (17)

-continued
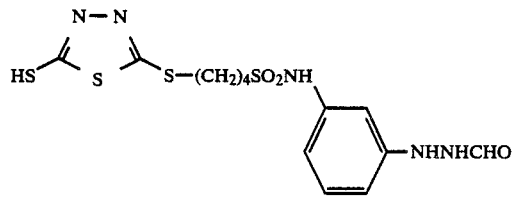 (18)
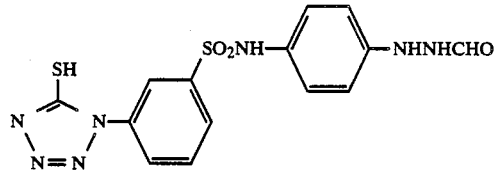 (19)
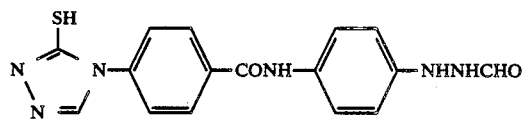 (20)
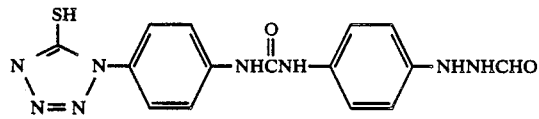 (21)
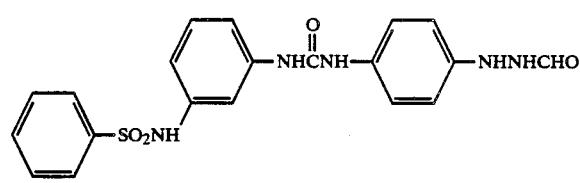 (22)
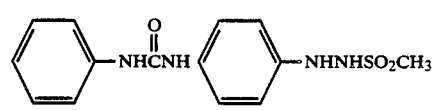 (23)
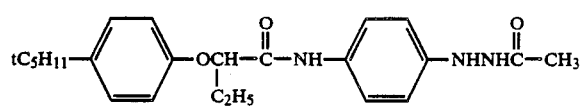 (24)
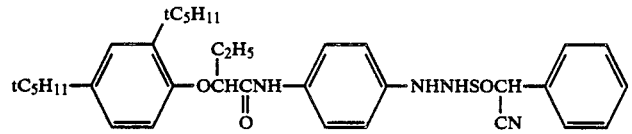 (25)
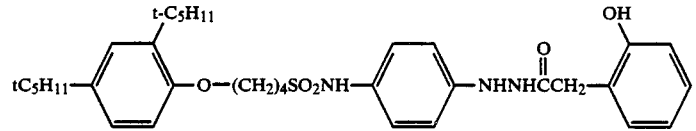 (26)
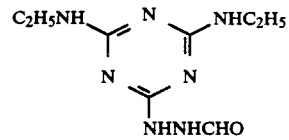 (27)

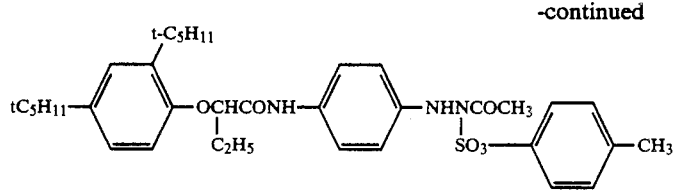

(28)

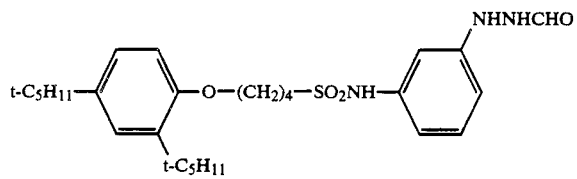

(29)

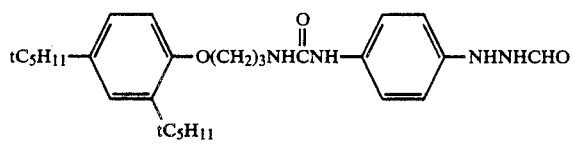

(30)

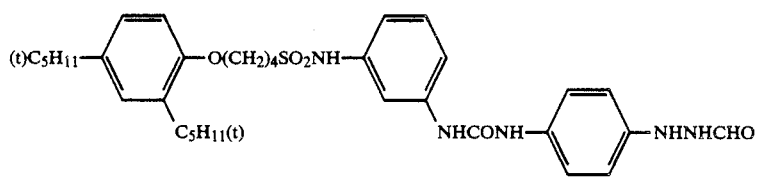

(31)

As the hydrazine derivatives to be used in the present invention, those which are described in *Research Disclosure*, Item 23516, Nov. 1983, p. 346 and literatures cited therein, U.S. Pat. Nos. 4,080,207, 4,269,929, 4,276,364, 4,278,748, 4,385,108, 4,459,347, 4,560,638, and 4,478,928, British Patent No. 2,011,391B, and JP-A- No. 60-179734 may be used in addition to the above-described compounds.

The compound represented by formula (IV) is incorporated in the silver halide layer in an amount of preferably from $1 \times 10^{-6}$ mol to $5 \times 10^{-2}$ mol, more preferably from $1 \times 10^{-5}$ mol to $2 \times 10^{-2}$ mol, per mol of silver halide.

The tetrazolium compounds to be used in the present invention typically include compounds reprecented by formulae (V), (VI), and (VII):

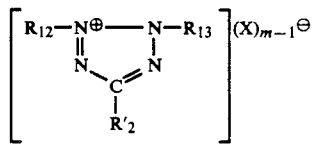

(V)

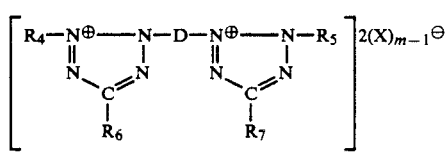

(VI)

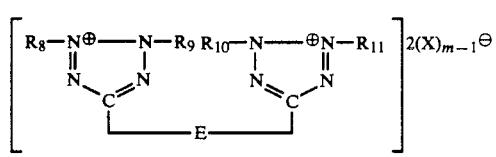

(VII)

wherein $R_{12}$, $R_{13}$, $R_4$, $R_5$, $R_8$, $R_9$, $R_{10}$, and $R_{11}$ each independently represents a group selected from among a substituted or unsubstituted alkyl group (for example, methyl, ethyl, hexyl, dodecyl, hydroxymethyl, chloroethyl), allyl group, a phenyl group (for example, phenyl, tolyl, hydroxyphenyl, carboxyphenyl, aminophenyl, mercaptophenyl), a naphthyl group (for example, α-naphthyl, β-naphthyl, hydroxynaphthyl, carboxynaphthyl, aminonaphthyl), and a heterocyclic group (for example, thiazolyl, benzothiazolyl, oxazolyl, pyrimidinyl, pyridyl), all of which may form a metal chelate or complex; $R'_2$, $R_6$, and $R_7$ each independently represents a group selected from among allyl group, a phenyl group, a naphthyl group, a heterocyclic group, an alkyl group (for example, methyl, ethyl, propyl, butyl, mercaptomethyl, mercaptoethyl), hydroxyl group, a carboxyl group or its salt, a carboxyalkyl group (for example, methoxycarbonyl, ethoxycarbonyl), an amino group (for example, amino, ethylamino, anilino), a mercapto group, a nitro group, and hydrogen atom; D represents a divalent aromatic group; E represents a group selected from among an alkylene gfoup, an arylene group, and an aralkylene group; X represents an anion to be described in detail hereinafter; and m represents 1 or 2, provided that m is 1 when the compound forms intramolecular salt.

Specific examples of the cation part of the tetrazolium compounds to be used in the present invention are illustrated below which, however, do not limit the compounds to be used in the present invention in any way.

(1) 2-(Benzothiazol-2-yl)-3-phenyl-5-dodecyl-2H-tetrazolium
(2) 2,3-Diphenyl-5-(4-t-octyloxyphenyl)-2H-tetrazolium
(3) 2,3,5-Triphenyl-2H-tetrazolium
(4) 2,3,5-Tri(p-carboxyethylphenyl)-2H-tetrazolium
(5) 2-(Benzothiazol-2-yl)-3-phenyl-5-(o-chlorophenyl)-2H-tetrazolium (6) 2,3-Diphenyl-2H-tetrazolium
(7) 2,3-Diphenyl-5-methyl-2H-tetrazolium
(8) 3-(p-Hydroxyphenyl)-5-methyl-2-phenyl-2H-tetrazolium
(9) 2,3-Diphenyl-5-ethyl-2H-tetrazolium
(10) 2,3-Diphenyl 5-n-hexyl-2H-tetrazolium
(11) 5-Cyano-2,3-diphenyl-2H-tetrazolium
(12) 2-(Benzothiazol-2-yl)-5-phenyl-3-(4-tolyl)-2H-tetrazolium
(13) 2-(Benzothiazol-2-yl)-5-(4-chlorophenyl)-3-(4-nitrophenyl)-2H-tetrazolium
(14) 5-Ethoxycarbonyl-2,3-di(3-nitrophenyl)-2H-tetrazolium

(15) 5-Acetyl-2,3-di(p-ethoxyphenyl)-2H-tetrazolium
(16) 2,5-Diphenyl-3-(p-tolyl)-2H-tetrazolium
(17) 2,5-Diphenyl-3 (p-iodophenyl)-2H-tetrazolium
(18) 2,3-Diphenyl-5-(p-diphenyl)-2H-tetrazolium
(19) 5-(p-Bromophenyl)-2-phenyl-3-(2,4,6trichlorophenyl)-2H-tetrazolium
(20) 3-(p-Hydroxyphenyl)-5-(p-nitrophenyl)-2-phenyl-2H-tetrazolium
(21) 5-(3,4-Dimethoxyphenyl)-3-(2-ethoxyphenyl)-2-(4-methoxyphenyl)-2H-tetrazolium
(22) 5-(4-Cyanophenyl)-2,3-diphenyl-2H-tetrazolium
(23) 3-(p-Acetamidophenyl)-2,5-diphenyl-2H-tetrazolium
(24) 5-Acetyl-2,3-diphenyl-2H-tetrazolium
(25) 5-(Fur-2-yl)-2,3-diphenyl-2H-tetrazolium
(26) 5-(Thien-2-yl)-2,3-diphenyl-2H-tetrazolium
(27) 2,3-Diphenyl-5-(pyrid-4-yl)-2H-tetrazolium
(28) 2,3-Diphenyl-5-(quinol-2-yl)-2H-tetrazolium
(29) 2,3-Diphenyl-5-(benzoxazol-2-yl)-2H-tetrazolium
(30) 2,3-Diphenyl-5-nitro-2H-tetrazolium
(31) 2,2',3,3'-Tetraphenyl-5,5'-1,4-butylene-di-(2H-tetrazolium
(32) 2,2',3,3'-Tetraphenyl-5,5'-p-phenylene-di-(2H-tetrazolium
(33) 2-(4,5-Dimethylthiazol-2yl)-3,5-diphenyl-2H-tetrazolium
(34) 3,5-Diphenyl-2-(triazin-2-yl)-2H-tetrazolium
(35) 2-(Benzothiazol-2-yl)-3-(4-methoxyphenyl)-5-phenyl-2H-tetrazolium
(36) 1-Methyl-2-phenyl-2H-1,2,3-triazolium
(37) 1-n-Propyl-2-phenyl-2H-1,2,3-triazolium
*38) 2-(4-Methoxyphenyl)-3-phenyl-2H-naphtho-[1,2-d]-1,2,3-triazolium
(39) 1,5-Di(9,10-anthraquinolyl)-bis-{2-[3-phenyl]-2H-naphtho-[1,2-d]-1,2,3-triazolium }
(40) 2,3-Di(4-methoxyphenyl)-5-nitro-2H-naphtho[1,2-d]-1,2,3-triazolium
(41) 2-(p-Iodophenyl)-3-(p-nitrophenyl)-5-phenyl-2H-tetrazolium
(42) 2-(p-Methylphenyl)-3,5-diphenyl-2H-tetrazolium
(43) 2,3-Di(p-methylphenyl)-5-phenyl-2H-tetrazolium
(44) 2,3,5-Tri(p-methylphenyl)-2H-tetrazolium
(45) 2,5-Di(p-methylphenyl)-3-(p-methoxyphenyl}-2H-1 tetrazolium
(46) 2,3,5-Tri(p-methoxyphenyl)-2H-tetrazolium
(47) 2-(p-Ethylphenyl}-3,5-diphenyl-2H-tetrazolium
(48) 2,3-Di(p-propylphenyl)-5-phenyl-2H-tetrazolium
(49) 2,3-Di(p-ethoxyphenyl)-5-phenyl-2H-tetrazolium
(50) 2,3-Di(p-n-dodecylphenyl)-5-phenyl-2H-tetrazolium As the anion represented by X, there are illustrated, for example, halide ions such as chloride ion, bromide ion and iodide ion, acid groups of inorganic acids such as sulfuric acid, nitric acid and perchloric acid, acid groups of organic acids such as sulfonic acids and carboxylic acids, lower alkylbenzenesulfonate anions such as p-toluenesulfonate anion, higher alkylbenzenesulfonate anions such as p-dodecylbenzenesulfonate anion, higher alkyl sulfates such as lauryl sulfate anion, dialkyl sulfosuccinate anions such as di-2-ethylhexyl sulfosuccinate anion, polyether alcohol sulfate anions such as cetyl polyethenoxysulfate anion, higher fatty acid anions such as stearic acid anion, and acid radical-containing polymers such as polyacrylic acid anion.

The non-diffusible tetrazolium compounds of the present invention may be synthesized by properly selecting the anion and the cation. The thus synthesized compounds of the present invention are, for example, a sulfonic acid salt of 2,3,5-triphenyl-2H-tetrazolium dioctylsuccinate. As will be described in detail in the Examples which follow, these compounds can be dispersed in a gelatin matrix in two ways. In one way, respective soluble salts are separately dispersed in gelatin, and the two dispersions are then mixed with each other and dispersed in a gelatin matrix. In another way, a synthesized non-diffusible tetrazolium compound, in pure form, is dissolved in a proper solvent (for example, dimethyl sulfoxide.) and dispersed in a gelatin matrix. Where the homogeneity of the dispersion is difficult to achieve, application of ultrasonic wave or use of a proper homogenizer such as a Manton Gorin homogenizer sometimes provides excellent results.

The tetrazolium compound is used in an amount of from about 0.001 mol to about 10 mols, preferably from about from 0.001 mol to 1 mol, per mol of silver halide incorporated in the light-sensitive material of the present invention.

As a binder or protective colloid for emulsion layers or interlayers of the light-sensitive materials of the present invention, gelatin is advantageously used. However, other hydrophilic colloids can be used as well. For example, proteins such as gelatin derivatives, graft polymers of gelatin and other high polymers, albumin, casein; cellulose derivatives such as hydroxyethyl cellulose, carboxymethyl cellulose, cellulose sulfate; sugar derivatives such as sodium alginate, starch derivative; and various synthetic hydrophilic macromolecular substances such as homopolymers or copolymers (e.g., polyvinyl alcohol, partially acetylated polyvinyl alcohol, poly-N-vinylpyrrolidone, polyacrylic acid, polymethacrylic acid, polyacrylamide, polyvinylimidazole, polyvinylpyrazole) may be used.

As gelatin, acid-processed gelatin or enzyme-processed gelatin as described in *Bull. Soc. Sci. Phot. Japan*, No. 16, p. 30 (1966) may be used as well as lime-processed gelatin. A gelatin hydrolyzate or an enzyme-decomposed product can also be used.

Photographic emulsions to be used in the present invention may be spectrally sensitized with methine dyes or the like. Dyes to be used include cyanine dyes, merocyanine dyes, complex cyanine dyes, complex merocyanine dyes, holopolar cyanine dyes, hemicyanine dyes, styryl dyes, and hemioxonol dyes. Particularly useful dyes include cyanine dyes, merocyanine dyes, and complex merocyanine dyes. These dyes may be so combined to obtain a supersensitizing effect.

Dyes which themselves do not have a spectrally sensitizing effect or substances which substantially do not absorb visible light and which show supersensitizing effects may be incorporated in the emulsion together with the sensitizing dye. For example, aminostilbene compounds substituted by a nitrogen-containing hetero ring group (for example, those described in U.S. Pat. Nos. 2,933,390 and 3,635,721), aromatic organic acid-formaldehyde condensates (for example, those described in U.S. Pat. No. 3,743,510), cadmium salts, and azaindene compounds may be incorporated therein. Combinations described in U.S. Pat. Nos. 3,615,613, 3,615,641, 3,617,295 and 3,635,721 are particularly useful.

In the photographic emulsion to be used in the present invention, various compounds for preventing fog or for stabilizing photographic properties during production, storage, or photographic processing of the light-sensitive material may be incorporated. That is, many compounds known as antifogging or stabilizing agents such as azoles (e.g., benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (particularly, 1-phenyl-5-mercaptotetrazole)); mercaptopyrimidines; mercaptotriazines; thioketo compounds (e.g., oxazolinethione); azaindenes (e.g., triazaindenes, tetraazaindenes (particularly, 4-hydroxy-subsituted (1,3,3a,7)tetraazaindenes), pentaazaindenes); benzenethiosulfonic acid; benzenesulfinic acid; and benzenesulfonamide may be added. Among these, benzotriazoles (e.g., 5-methylbenzotriazole) are particularly preferred. These compounds may also be incorporated in a processing solution.

The photographic light-sensitive material of the present invention may also contain inorganic or organic hardeners in the hydrophilic colloidal layers. For example, chromium salts (e.g., chromium alum, chromium acetate), aldehydes (e.g., formaldehyde, glyoxal, glutaraldehyde), N-methylol compounds (e.g., dimethylolurea, methyloldimethylhydantoin), dioxane derivatives (e.g., 2,3-dihydroxydioxane), active vinyl compounds (e.g., 1,3,5-triacryloyl-hexahydro-s-triazine, 1,3-vinylsulfonyl-2-propanol), active halogen compounds (e.g., 2,4-dichloro-6-hydroxy-s-triazine), and mucohalogenic acids (e.g., mucochloric acid, mucophenoxychloric acid) may be used alone or in combination.

The photographic emulsion layers or other hydrophilic colloidal layers may also contain various known surface active agents for various purposes such as coating aid, antistatic purpose, improvement of sliding property, emulsified dispersion, anti-adhesive purpose, and improvement of photographic properties (e.g., acceleration of development, increase in contrast, sensitization).

For example, there can be used nonionic surface active agents such as saponin (steroid series), alkylene oxide derivatives (e.g., polyethylene glycol, polyethylene glycol/polypropylene glycol condensate, polyethylene glycol alkyl or alkylaryl ethers, polyethylene glycol esters, polyethylene glycol sorbitan esters, polyalkylene glycol alkylamines or amides, polyethylene oxide adducts of silicone), glycidol derivatives (e.g., alkenylsuccinic acid polyglycerides, alkylphenol polyglycerides), fatty acid esters of polyhydric alcohols, and sugar alkyl esters; anionic surface active agents containing acid groups (such as carboxyl group, sulfo group, phospho group, sulfate group, phosphate group) such as alkylcarboxylic acid salts, alkylsulfonic acid salts, alkylbenzenesulfonic acid salts, alkylnaphthalenesulfonic acid salts, alkylsulfuric esters, alkylphosphoric esters, N-acyl-N-alkyltaurines, sulfosuccinic esters, sulfoalkylpolyoxyethylene alkylphenyl ethers, and polyoxyethylene alkylphosphates; amphoteric surface active agents such as amino acids, aminoalkylsulfonic acids, aminoalkylsulfuric or phosphoric esters, alkylbetaines, and amine oxides; and cationic surface active agents such as alkylamines, aliphatic or aromatic quaternary ammonium salts, heterocyclic quaternary ammonium salts (e.g., pyridinium, imidazolium), and aliphatic or hetero ring-containing phosphonium or sulfonium salts. Surfactants more preferably used in the present invention are polyalkylene oxides of 600 or more in molecular weight described in JP-B- No. 58-9412 (the term "JP-B" as used herein means an "examined Japanese patent publication").

The photographic light-sensitive material to be used in the present invention may contain in its photographic emulsion layers or other hydrophilic colloidal layers a dispersion of a water-insoluble or sparingly soluble synthetic polymer for the purpose of improving dimensional stability, etc. For example, there can be used homo- or copolymers of alkyl (meth)acrylates, alkoxyalkyl (meth)acrylates, glycidyl (meth)acrylate, (meth)acrylamide, vinyl esters (e.g., vinyl acetate), acrylonitrile, olefins, and styrene, or polymers containing as monomer components, combinations of the above-described monomers and, e.g., acrylic acid, methacrylic acid, $\alpha,\beta$-unsaturated dicarboxylic acids, hydroxyalkyl (meth)acrylates, sulfoalkyl (meth)acrylates, styrenesulfonic acid.

The present invention is illustrated in greater detail by reference to the following examples which, however, are not to be construed as limiting the present invention in any way. Unless stated otherwise, all parts, percents, ratios and the like are by weight.

EXAMPLE 1

Developers (A), (B) and (C) having the following formulations were prepared.

Developer (A)

| | |
|---|---|
| Sodium sulfite | 67 g |
| Hydroquinone | 23 g |
| 4-Hydroxymethyl-4-methyl-1-phenyl-3-pyrazolidone | 0.4 g |
| Potassium hydroxide | 11 g |
| Sodium carbonate | 11 g |
| Potassium bromide | 3.0 g |
| Illustrative compound 2 | 0.34 g |
| Water to make | 1 liter |
| pH | adjusted to 10.65 (with KOH) |

Developer (B) (Comparative Solution)

A developer having the same formulation as developer (A) was prepared, except that illustrative compound 2 was not added.

Developer (C) (Comparative Solution)

A developer having the same formulation as developer (A) was prepared, except that 0.164 g of 2-mercapto-5-methylmercapto-1,3,4-thiadiazole per liter of developer were added in place of the illustrative compound 2.

Illustrative compound 2

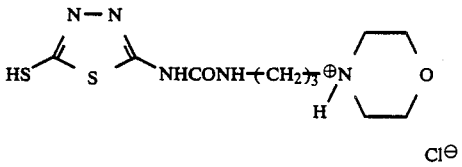

Films were prepared in the following manner.
Solution I: water 600 ml; gelatin 18 g; pH 3.0
Solution II: AgNO3 200 g; water 800 ml
Solution III: KBr 42 g; NaCl 52 g; NH4RhC16 40 mg; water 800 ml.

Solution II and Solution III were simultaneously added at a constant rate to Solution I which was kept at 42° C. over 30 minutes. After removing soluble salts from the emulsion in a conventional manner well known in the art, gelatin was added to the solution and, without chemical ripening, 2-methyl-4-hydroxy-1,3,3a,7-tetraazaindene was added thereto as a stabilizer. The grains in this emulsion had an average grain size of 0.25 μm. 1 kg of the emulsion was obtained, wherein the content of gelatin was 60 g. To this emulsion, 3-carboxymethyl-5-[2-(3-ethylthiazolidin-2-yliden-)ethyliden]rhodanine was added as a sensitizing dye, sodium dodecylbenzenesulfonate was added as a surfactant, 2-hydroxy-4,6-dichloro-1,3,5-triazine sodium salt was added as a hardener, and a dimensional stabilizing agent and a thickening agent were added, followed by coating the resulting mixture in a silver amount of 3.8 g/m² on a polyethylene terephthalate support. Further, a gelatin aqueous solution containing polymethyl methacrylate and a surfactant was coated onto as a protective layer in a gelatin amount of 1.0 g/m² to obtain Film No. 1.

The following experiment was conducted with respect to developers (A), (B) and (C). 20.5 liters of the developer were placed in a roller-conveying type automatic developing machine (FGB-660F; made by Fuji Photo Film Co., Ltd.), and imagewise exposed Film No. 1 was introduced into the developer to develop the same. The developing temperature and developing time were 38° C. and 20 seconds, respectively, and the developer was replenished automatically at a rate of 100 ml per development of one full-size sheet (20 in. ×24 in.).

100 films of full-size sheet were developed for 5 hours a day, and this procedure was continued for one week. With developers (B) and (C) not containing the compound of the present invention, the initially colorless and transparent developers shortly became turbid during development of the first 100 films, and deposition of silver sludge was observed next day. Streamlike silver stains began to appear on the processed films. The stains became more and more pronounced during the one-week processing. The developers became excessively turbid, with large amounts of silver sludge deposited therein. Excessive silver stain was also observed on rollers of the automatic developing machine. The stream-like silver stains on the processed films became more serious as the number of processed films increased.

The processed film surface was observed to have flaws supposedly formed by the contact with sludge deposited on rollers.

On the other hand, developer (A) containing the compound of the present invention maintained its initial colorless, transparent state even after the one-week development processing. No silver sludge was observed, and silver stain or flaws on the processed film surface were not observed at all.

EXAMPLE 2

Developers (D), (E) and (F) having the following formulations were prepared.

Developer (D)

| | |
|---|---|
| Potassium sulfite | 110.0 g |
| Hydroquinone | 50.0 g |
| N-Methyl-p-aminophenol ½ sulfate | 0.3 g |
| Sodium hydroxide | 18.0 g |
| 5-Sulfosalicylic acid | 55.0 g |
| Disodium ethylenediaminetetraacetate | 1.0 g |
| Potassium bromide | 10.0 g |
| 5-Methylbenzotriazole | 0.4 g |
| Sodium toluenesulfonate | 8.0 g |
| Sodium 3-(5-mercaptotetrazole)benzenesulfonate | 0.2 g |
| N-n-Butyl diethanolamine | 15.0 g |
| Illustrative compound 4 | 0.34 g |
| Water to make | 1 liter |
| pH | adjusted to 11.6 (by adding KOH) |

Developer (E) (Comparative Solution)

A developer having the same formulation as developer (D) was prepared, except that illustrative compound 4 was not added.

Developer (F) (Comparative Solution)

A developer having the same formulation as developer (D) was prepared, except that 0.314 g of 2-mercapto-5-(3-morpholino)propylthio-1,3,4-thiadiazole hydrochloride per liter of developer were added in place of illustrative compound 4.

llustrative compound 4

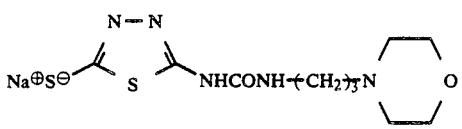

Films were prepared in the following manner.

A silver nitrate aqueous solution and a sodium chloride aqueous solution containing $5 \times 10^{-6}$ mol of ammonium hexachlororhodate (III) per mol of silver were mixed in a 40° C. gelatin solution according to the double jet process with controlling pH at 2.3 to prepare a monodispersed silver chloride emulsion of 2.0 μm in average grain size.

After formation of grains, soluble salts were removed according to the flocculation process well known in the art. Then, 4-hydroxy-6-methyl-1,3,3a,7-tetrazaindene and 1-phenyl-5-mercaptotetrazole were added thereto as stabilizers. The emulsion contained 55 g of gelatin and 105 g of silver per kg.

The following compound (Z) was added to this emulsion in an amount of 70 mg/m², and 2,4-dichloro-6-hydroxy-1,3,5-triazine sodium salt was added thereto as a hardener. The resulting emulsion was coated in a silver amount of 3.5 g/m² on a polyethylene terephthalate transparent support to form a silver halide emulsion layer, and a gelatin layer was coated thereon as a protective layer to prepare Film No. 2.

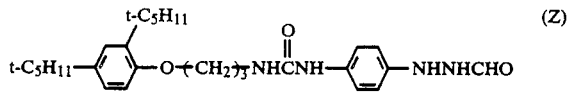

The following experiment was conducted using developers (D), (E) and (F). 20.5 liters of the developer were placed in a roller-conveying type automatic developing machine (FG-660F; made by Fuji Photo Film Co., Ltd.), and imagewise exposed Film No. 2 was introduced into the developer to develop. The developing temperature and developing time were 38° C. and 20 seconds, respectively, and the developer was replenished automatically at a rate of 75 ml per development of one full-size sheet (20 in. ×24 in.).

100 films of full-size sheet were developed for 5 hours a day, and this procedure was continued for one week. With developers (E) and (F) not containing the compound of the present invention, the initially colorless and transparent developers became turbid, and deposition of silver sludge was observed next day. Stream-like silver strains began to appear on the processed films. The stains became more and more pronounced during the one-week processing. The developer became excessively turbid, with large amounts of silver sludge deposited therein. Excessive silver stain was also observed on rollers of the automatic developing machine. The stream-like silver stains on the processed films became more serious as the number of processed films increased.

The processed film surface wa observed to have flaws supposedly formed by the contact with sludge deposited on rollers.

On the other hand, developer (D) containing the compound of the present invention maintained its initial colorless, transparent state even after the one-week development processing. No silver sludge was observed, and silver stain or flaws on the processed film surface were not observed at all.

EXAMPLE 3

Developers (G), (H) and (I) having the following formulations were prepared.

| | |
|---|---|
| Disodium ethylenediaminetetraacetate (dihydrate) | 0.75 g |
| Anhydrous potassium sulfite | 51.7 g |
| Anhydrous potassium carbonate | 60.4 g |
| Hydroquinone | 15.1 g |
| 1-Phenyl-3-pyrazolidone | 0.51 g |
| Sodium bromide | 2.2 g |
| 5-Methylbenzotriazole | 0.124 g |
| 1-Phenyl-5 mercaptotetrazole | 0.018 g |
| 5-Nitroindazole | 0.106 g |
| Diethylene glycol | 98.0 g |
| Illustrative compound 8 | 0.34 g |
| Water to make | 1 liter |
| pH | adjusted to 10.5 (with KOH) |

Developer (H) (Comparative solution)

A developer having the same formulation as developer (G) was prepared, except that illustrative compound 8 was not added.

Developer (I) (Comparative solution)

A developer having the same formulation as developer (G) was prepared, except that 0.190 g of 2-mercapto-5-(3-methylureido)-1,3,4-thiadiazole per liter of the developer in place of illustrative compound 8 were added.

Illustrative compound 8

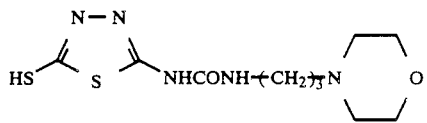

Films were prepared in the following manner.

A silver chlorobromide emulsion was prepared by using the following solutions l, m and n.

| | |
|---|---|
| (Solution l) | |
| Ossein gelatin | 17 g |
| 10% Ethanol solution of polyisopropylene-polyethyleneoxydisuccinate sodium salt | 5 ml |
| Distilled water | 1280 cc |
| (Solution m) | |
| Silver nitrate | 170 g |
| Distilled water | 410 ml |
| (Solution n) | |
| Sodium chloride | 74.81 g |
| Potassium bromide | 2.39 g |
| Ossein gelatin | 11 g |
| Rhodium trichloride trihydrate | 5 mg |
| 10% Ethanol solution of polyiso-propylene-polyethyleneoxydisuccinate sodium salt | 3 ml |
| Distilled water | 412 ml |

The water-soluble rhodium salt was added to solution n in an amount of 5 mg/AgX as $RhCl_3 \cdot 3H_2O$, i.e., $1.9 \times 10^{-5}$ mol/mol AgX.

Solution m and solution n were added to solution l according to the simultaneously mixing process under the following conditions. The temperature was kept during the addition at 40° C., the time for the addition of solution m and solution n was 40 minutes, the Ostwald ripening time after the addition was 10 minutes, and the temperature of the ripening was 40° C. The conditions were selected so as to prepare silver halide grains having an average grain size of 0.20 μm and having such grain size distribution that 90% or more grains were within ±0.05 μm of the average grain size. After the Ostwald ripening, desalting and water-washing were conducted in a conventional manner. Then, 6-methyl-4-hydroxy-1,3,3a,7-tetrazaindene was added in an amount of 1 g/mol AgX, 2,3-di(p-methylphenyl)-5-phenyl-tetrazolium chloride (a tetrazolium compound) in an amount of 1.0 g/mol AgX, styrene-butyl acrylate latex polymer was added in an amount of 2 g/m², gelatin was added in an amount of 1.3 g/m², and AgX grains were added in a silver amount of 3.5 g/m². This emulsion layer was coated in a gelatin amount of 1.5 g/m² using a saponin solution as a spreading solution simultaneously with a protective film containing 10 mg of sodium 2,4-dichlorotriazine sodium salt per gram of gelatin using bis(2-ethylhexyl)sulfosuccinate as a spreading agent onto a polyethylene terephthalate support. The resulting film was referred to as Film No. 3.

The following experiment was conducted using developers (G), (H) and (I). 20.5 liters of the developer were placed in a roller-conveying type automatic developing machine (FG-660F; made by Fuji Photo Film Co., Ltd.), and imagewise exposed film No. 3 was introduced into the developer to develop. The developing temperature and developing time were 28° C. and 30 seconds, respectively, and the developer was replenished automatically at a rate of 120 ml per development of one full-size sheet (20 in.×24 in.).

100 films of full-size sheet were developed for 5 hours a day, and this procedure was continued for one week. With developers (H) and (I) not containing the compound of the present invention, initially colorless and transparent developers became turbid on the second day, and serious turbidity and deposition of silver sludge were observed. Rollers of the automatic developing machine were also seriously stained with silver.

On the other hand, developer (G) containing the compound of the present invention maintained its initial colorless and transparent state after the one-week development processing and no silver sludge was observed.

While the invention has been described in detail and with reference to specific embodiments thereof, it will be apparent to one skilled in the art that various changes and modifications can be made therein without departing from the spirit and scope thereof.

What is claimed is:

1. A process for development-processing an imagewise exposed black-and-white silver halide light-sensitive material, comprising using a developer containing at least one compound represented by formula (I) or (II):

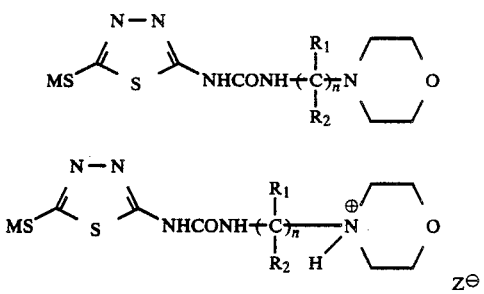

wherein
$R_1$ and $R_2$ each represents a hydrogen atom, an alkyl group or an aryl group;
M represents a hydrogen atom, an alkali metal atom, a quaternary ammonium salt, a quaternary phosphonium salt, an amidino group or a group capable of being converted to hydrogen or an alkali metal atom under alkaline conditions;
n represents an integer of 1 or more; and
$Z^{\ominus}$ represents an anion.

2. A process as claimed in claim 1, wherein said at least one compound is present in said developer in an amount from $1\times 10^{-2}$ to $1\times 10^{-5}$ mol/liter.

3. A process as claimed in claim 1, wherein said developer further comprises a 3-pyrazolidone developing agent.

4. A process as claimed in claim 1, wherein said developer further comprises an alkali metal sulfite such that the amount of free sulfite ion is 13 grams or more per liter of said developer.

5. A process as claimed in claim 1, wherein said developer further comprises a compound represented by general formula (III):

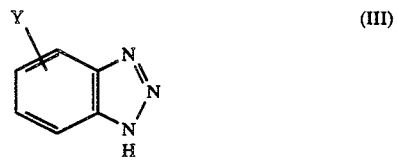

wherein Y represents a hydrogen atom, a halogen atom, an acetylamino group containing from 2 to 10 carbon atoms, or an alkyl group containing from 1 to 10 carbon atoms.

6. A process as claimed in claim 5, wherein said compound represented by general formula (III) is present in said developer in an amount of $1\times 10^{-5}$ mol/liter to $1\times 10^{-2}$ mol/liter.

7. A process as claimed in claim 1, wherein said developer is maintained at a temperature of from 181° C. to 50° C.

8. A process as claimed in claim 1, wherein said photographic material is subjected to rapid processing whereby the processing time is no more than 2 minutes.

9. A process as claimed in claim 1, wherein said light-sensitive material comprises a hydrazine derivative or a tetrazolium derivative.

* * * * *